US011047782B1

(12) United States Patent
Zheng et al.

(10) Patent No.: US 11,047,782 B1
(45) Date of Patent: Jun. 29, 2021

(54) TEST APPARATUS AND METHOD FOR SIMULATING SEISMIC DYNAMIC RESPONSE OF UNDERGROUND CAVERN

(71) Applicant: INSTITUTE OF GEOLOGY AND GEOPHYSICS, CHINESE ACADEMY OF SCIENCES, Beijing (CN)

(72) Inventors: Bowen Zheng, Beijing (CN); Shengwen Qi, Beijing (CN); Qian Sheng, Beijing (CN); Xiaolin Huang, Beijing (CN); Ning Liang, Beijing (CN); Songfeng Guo, Beijing (CN); Guangming Luo, Beijing (CN); Chonglang Wang, Beijing (CN); Wenjiao Xiao, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/185,972

(22) Filed: Feb. 26, 2021

(30) Foreign Application Priority Data

Apr. 23, 2020 (CN) .......................... 202010325289.X

(51) Int. Cl.
*G01N 3/04* (2006.01)
*G01N 33/24* (2006.01)

(52) U.S. Cl.
CPC .............. *G01N 3/04* (2013.01); *G01N 33/24* (2013.01); *G01N 2203/0075* (2013.01); *G01N 2203/0246* (2013.01)

(58) Field of Classification Search
CPC ............ G01N 33/24; G01N 3/12; G01N 3/04; G01N 1/28; G01N 3/307; G01N 3/06;
(Continued)

(56) References Cited

U.S. PATENT DOCUMENTS

| 10,408,718 B2* | 9/2019 | Zhang ...................... G01N 3/12 |
| 2003/0172739 A1* | 9/2003 | Horiuchi ............... G01M 7/025 |
| | | 73/662 |

(Continued)

FOREIGN PATENT DOCUMENTS

| CN | 104899678 A | 9/2015 |
| CN | 105137031 A | 12/2015 |

(Continued)

OTHER PUBLICATIONS

Jin-Yu Dong, et al., The large-scale shaking table test study of dynamic response and failure mode of bedding rock slope under earthquake, Rock and Soil Mechanics, 2011, vol. 32 No. 10.

*Primary Examiner* — Brandi N Hopkins
(74) *Attorney, Agent, or Firm* — Bayramoglu Law Offices LLC

(57) ABSTRACT

A test apparatus for simulating a seismic dynamic response of an underground cavern includes a loading frame, an overlying model and an underlying model of the underground cavern, a static loading device, a dynamic loading device and a measuring device. A vertical load and a horizontal load are separately applied by the static loading device to the overlying model to simulate real vertical and horizontal in-situ stresses of the in-situ underground cavern. A seismic dynamic load is applied by the dynamic loading device to the underlying model, and then acts on the overlying model to simulate a real seismic ground motion on the in-situ underground cavern. In this way, the present invention satisfies simulation requirements for the seismic dynamic response of the underground cavern to implement a high-fidelity simulation on the underground cavern through unified loading of the in-situ stress static load and the seismic dynamic load.

13 Claims, 2 Drawing Sheets

(58) Field of Classification Search
CPC ... G01B 21/32; H02J 7/35; H02J 7/00; H01M 10/615; G06F 30/20; G06F 111/10; G06F 119/14
See application file for complete search history.

(56) References Cited

U.S. PATENT DOCUMENTS

2015/0061669 A1* 3/2015 Hakimuddin .......... G01R 33/28
                                                    324/309
2015/0338549 A1   11/2015 Li et al.

FOREIGN PATENT DOCUMENTS

| CN | 106226112  | A  | 12/2016 |
|----|------------|----|---------|
| CN | 106596294  | A  | 4/2017  |
| CN | 107228803  | A  | 10/2017 |
| JP | 2009052264 | A  | 3/2009  |
| JP | 4558650    | B2 | 10/2010 |

* cited by examiner

TEST APPARATUS AND METHOD FOR SIMULATING SEISMIC DYNAMIC RESPONSE OF UNDERGROUND CAVERN

CROSS REFERENCE TO THE RELATED APPLICATIONS

This application is based upon and claims priority to Chinese Patent Application No. 202010325289.X, filed on Apr. 23, 2020, the entire contents of which are incorporated herein by reference.

TECHNICAL FIELD

The present invention belongs to the field of large-scale physical model tests of rock mass dynamics, and specifically relates to a test apparatus and method for simulating a seismic dynamic response of an underground cavern.

BACKGROUND

An underground cavern mainly includes surrounding rock, a lining and an internal space. The stability of the surrounding rock of underground caverns is one of the classic problems in the fields of engineering geology and rock mechanics. The loads are divided into static loads and dynamic loads. Dynamic loads acting on underground caverns include seismic loads, blasting loads, and mechanical vibration loads. The analysis of the dynamic response of underground caverns under seismic dynamic loads, that is, response characteristics such as deformation and strength of the underground caverns under seismic conditions, has become one of the active areas of research in engineering geology, rock and soil mechanics, and seismic engineering.

At present, seismic dynamic responses of underground caverns are typically studied by numerical simulation methods. These numerical simulation methods, however, lack measured data of the seismic dynamic response of underground caverns, and thus still need to prove the rationality of the numerical simulation results. The shaking table model test is an effective approach in studying the seismic dynamic response and evaluating the seismic stability in engineering. Shaking table model tests are widely used in various fields such as seismic dynamic response research, stability evaluation and earthquake prevention and control of rock slopes. However, this test method has not yet been popularized in the study of the seismic dynamic response of underground caverns. This is because the prior art fails to perform high-fidelity simulations on the underground caverns through unified loading of the in-situ stress static load and the seismic dynamic load, which restricts the research process of the seismic dynamic response of underground caverns.

SUMMARY

In order to solve the problem that the prior art fails to perform high-fidelity simulation on the seismic dynamic response of underground caverns, the present invention provides a test apparatus and method for simulating a seismic dynamic response of an underground cavern.

The first aspect of an embodiment of the present invention provides a test apparatus for simulating a seismic dynamic response of an underground cavern, including a loading frame, an underground cavern model, a static loading device, a dynamic loading device and a measuring device.

The underground cavern model is a similar material model, including an overlying model and an underlying model. The overlying model is provided on the top of the underlying model. The overlying model and the underlying model constitute a convex structure.

The static loading device includes a normal loading device and a lateral loading device. The normal loading device is provided on the top of the overlying model, and the upper end of the normal loading device is connected to a top plate of the loading frame. The lateral loading device is provided on the peripheral side of the overlying model, and an end of the lateral loading device away from the overlying model is connected to a side plate of the loading frame.

The dynamic loading device includes a model box, a bearing table and a dynamic load driving device for driving the model box and the bearing table to vibrate. The model box is provided on the bearing table. A chamber for receiving the underlying model is provided inside the model box.

The measuring device includes a load measuring device and a deformation measuring device. The load measuring device includes a normal load measuring device for measuring a load value of the top of the overlying model and a lateral load measuring device for measuring a load value of the peripheral side of the overlying model. The deformation measuring device includes a normal deformation measuring device for measuring a deformation value of the top of the overlying model and a lateral deformation measuring device for measuring a deformation value of the peripheral side of the overlying model.

In some preferred embodiments, a hole for simulating an in-situ underground cavern is provided in the overlying model, and the hole is a through hole.

In some preferred embodiments, the overlying model is provided directly above the underlying model, and the overlying model and the underlying model are cemented by a model material.

In some preferred embodiments, the underlying model and the model box have the same height, and the peripheral side of the underlying model is connected to the model box by silica gel.

In some preferred embodiments, the normal load measuring device is a normal load sensor, and the lateral load measuring device is a lateral load sensor.

The normal loading device includes a normal driving device and a normal backing plate. The normal backing plate is a steel backing plate. The normal driving device is provided on the top plate of the loading frame, and a loading end of the normal driving device applies a force to the top of the overlying model through the normal backing plate.

The lateral loading device includes a lateral driving device and a lateral backing plate. The lateral backing plate is a steel backing plate. The lateral driving device is provided on the side plate of the loading frame, and a loading end of the lateral driving device applies a force to the side wall of the overlying model through the lateral backing plate.

In some preferred embodiments, the normal driving device is a normal cylinder, and the normal cylinder is fixed at the center of the top plate of the loading frame.

The lateral driving device is a lateral cylinder. The lateral cylinder includes a left cylinder, a right cylinder, a front cylinder and a rear cylinder. The left cylinder, the right cylinder, the front cylinder and the rear cylinder are fixed at the centers of a left side plate, a right side plate, a front side plate and a rear side plate of the loading frame, respectively.

In some preferred embodiments, the normal deformation measuring device is normal deformation sensors. One end of the normal deformation sensor is fixed to the top of the loading frame, and the other end of the normal deformation sensor is in contact with the normal backing plate.

The number of the normal deformation sensors is four, and the four normal deformation sensors are symmetrically arranged around the normal cylinder.

The lateral deformation measuring device is lateral deformation sensors. One end of the lateral deformation sensor is fixed to a side plate of the loading frame, and the other end of the lateral deformation sensor is in contact with the lateral backing plate.

The lateral deformation sensors include two left deformation sensors, two right deformation sensors, two front deformation sensors and two rear deformation sensors. The left deformation sensors, the right deformation sensors, the front deformation sensors and the rear deformation sensors are symmetrically arranged on both sides of the left cylinder, the right cylinder, the front cylinder and the rear cylinder, respectively, and are configured to measure deformation values of the left side, the right side, the front side and the rear side of the overlying model, respectively.

In some preferred embodiments, the model box is an uncovered cuboid steel box structure. The model box and the bearing table are fixedly connected by a bolt.

In some preferred embodiments, the test apparatus further includes a numerical control device. The numerical control device is communicatively connected to the static loading device and the dynamic loading device, and is configured to record the load value and the deformation value of the underground cavern model in real time.

A second aspect of the embodiment of the present invention provides a method based on the test apparatus for simulating a seismic dynamic response of an underground cavern, including the following steps:

S100: presetting a normal load value, a first horizontal load value, a second horizontal load value, a seismic dynamic load value, a seismic dynamic loading time value, a normal deformation threshold and a lateral deformation threshold;

S200: controlling the normal cylinder to apply a vertical load to the overlying model and keep the vertical load constant to simulate a real vertical in-situ stress of an in-situ underground cavern;

S300: controlling the front cylinder and the rear cylinder to separately apply a same first horizontal load to the overlying model and keep the first horizontal load constant to simulate a real larger horizontal in-situ stress of the in-situ underground cavern;

S400: controlling the left cylinder and the right cylinder to separately apply a same second horizontal load to the overlying model and keep the second horizontal constant to simulate a real smaller horizontal in-situ stress of the in-situ underground cavern;

S500: controlling the dynamic load driving device to apply a seismic dynamic load to the underlying model and allowing the seismic dynamic load to act on the overlying model through the underlying model to simulate a real seismic ground motion on the in-situ underground cavern; and S600: performing, by the numerical control device, real-time control on the test based on a load value and a deformation value of the overlying model acquired in real time by the normal load sensor, the lateral load sensor, the normal deformation sensor and the lateral deformation sensor during the test; stopping the test and exporting load and deformation test data when a seismic dynamic loading time reaches a preset value or when a normal deformation value or a lateral deformation value of the overlying model reaches the normal deformation threshold or the lateral deformation threshold.

The present invention has the following advantages.

1) The present invention provides a test apparatus for simulating a seismic dynamic response of an underground cavern, based on a similarity theory, a vertical load, a horizontal load and a seismic dynamic load are applied to the similar material model of the underground cavern through the static loading device and the dynamic loading device to simulate a seismic ground motion on the in-situ underground cavern under real vertical and horizontal in-situ stresses while accurately reflecting the in-situ conditions.

2) By using the test apparatus for simulating a seismic dynamic response of an underground cavern based on the similarity theory, materials in the similar material model of the underground cavern are proportioned according to different mass ratios to simulate the seismic dynamic response of the in-situ underground cavern under different geological environments, thereby satisfying different research needs.

3) The present invention features simple structure, novelty, safety, low cost, high-fidelity simulation and easy popularization, and has important theoretical and application value for evaluating the dynamic stability of underground caverns.

BRIEF DESCRIPTION OF THE DRAWINGS

Other features, objectives and advantages of the present invention will become more apparent upon reading the detailed description of the non-restrictive embodiments of the present invention with reference to the drawings.

Figure 1:
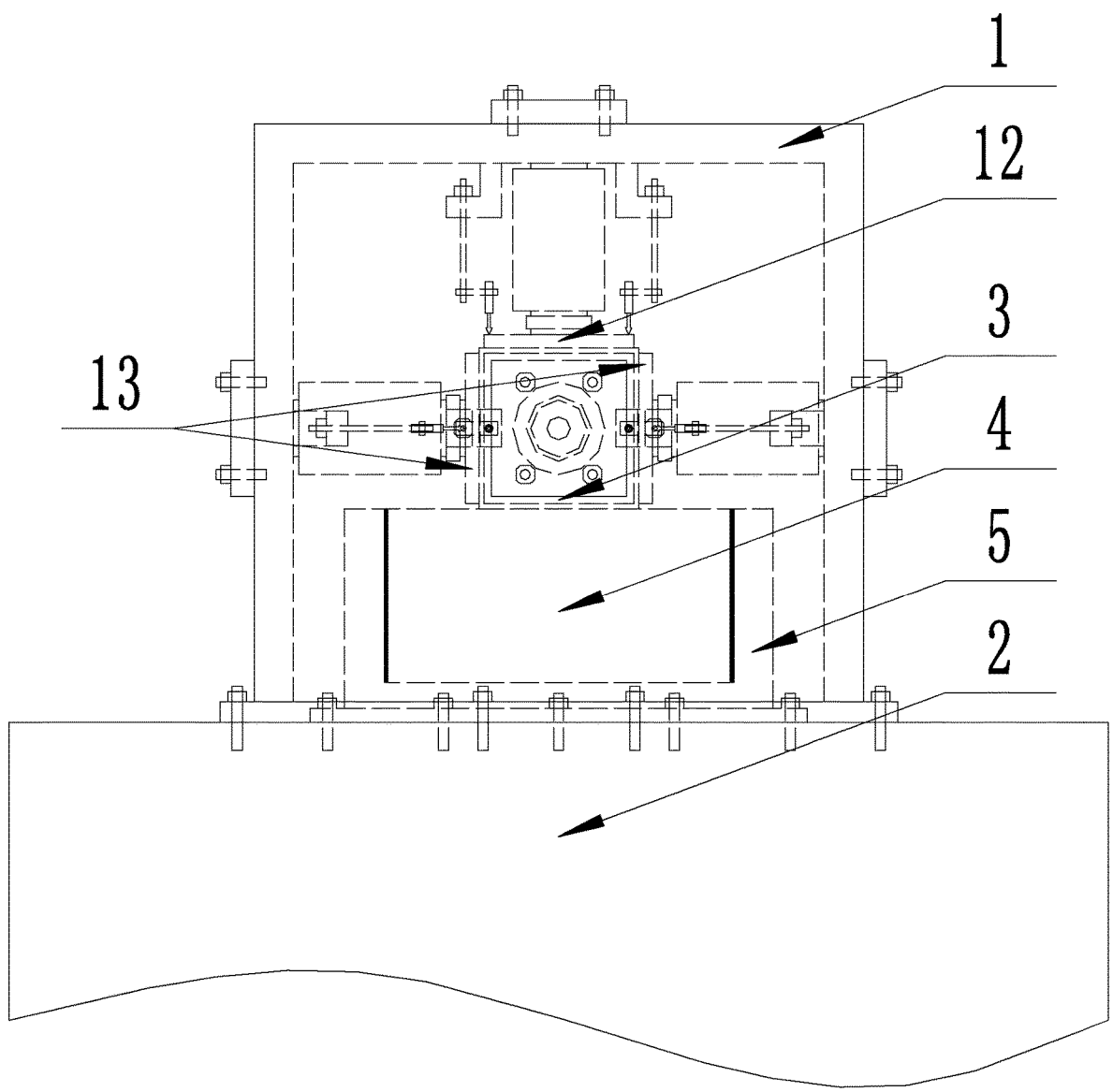
FIG. 1 is a front view of a test apparatus for simulating a seismic dynamic response of an underground cavern in a specific embodiment according to the present invention.

Reference numerals: 1. loading frame; 2. shaking table; 3. overlying model; 4. underlying model; 5. model box; 61. left cylinder; 62. right cylinder; 63. front cylinder; 64. rear cylinder; 71. left load sensor; 72. right load sensor; 73. front load sensor; 74. rear load sensor; 81. left deformation sensor; 82. right deformation sensor; 83. front deformation sensor; 84. rear deformation sensor; 9. normal deformation sensor; 10. normal cylinder; 11. normal load sensor; 12. normal backing plate; and 13. lateral backing plate.

DETAILED DESCRIPTION OF THE EMBODIMENTS

The preferred implementations of the present invention are described below with reference to the drawings. Those skilled in the art should understand that the implementations herein are merely intended to explain the technical principles of the present invention, rather than to limit the scope of protection of the present invention.

The present invention provides a test apparatus for simulating a seismic dynamic response of an underground cavern. The test apparatus includes a loading frame, an underground cavern model, a static loading device, a dynamic loading device and a measuring device. The underground cavern model includes an overlying model and an underlying model. The overlying model is provided on the top of the underlying model. The overlying model and the underlying model constitute a convex structure. The static loading device includes a normal loading device and a lateral loading device. The normal loading device is provided on the top of the overlying model, and the upper end of the normal loading device is fixedly connected to a top plate of the loading frame. The lateral loading device is provided on the peripheral side of the overlying model, and an end of the lateral loading device away from the overlying model is connected to a side plate of the loading frame. The dynamic loading device includes a model box, a bearing table and a dynamic load driving device for driving the model box and the bearing table to vibrate. The model box is provided on the bearing table. A chamber for receiving the underlying model is provided inside the model box. The measuring device includes a load measuring device and a deformation measuring device. The load measuring device includes a normal load measuring device for measuring a load value of the top of the overlying model and a lateral load measuring device for measuring a load value of the peripheral side of the overlying model. The deformation measuring device includes a normal deformation measuring device for measuring a deformation value of the top of the overlying model and a lateral deformation measuring device for measuring a deformation value of the peripheral side of the overlying model. By configuring the underground cavern model as a convex structure and placing the underlying model inside the model box, static loading and dynamic loading can be simultaneously performed on the underground cavern model to implement a high-fidelity simulation test on the seismic ground motion of the in-situ underground cavern under real vertical and horizontal in-situ stresses, while acquiring high-fidelity simulation test data.

The present invention is further described in detail below with reference to the drawings and specific embodiments.

Figure 2:
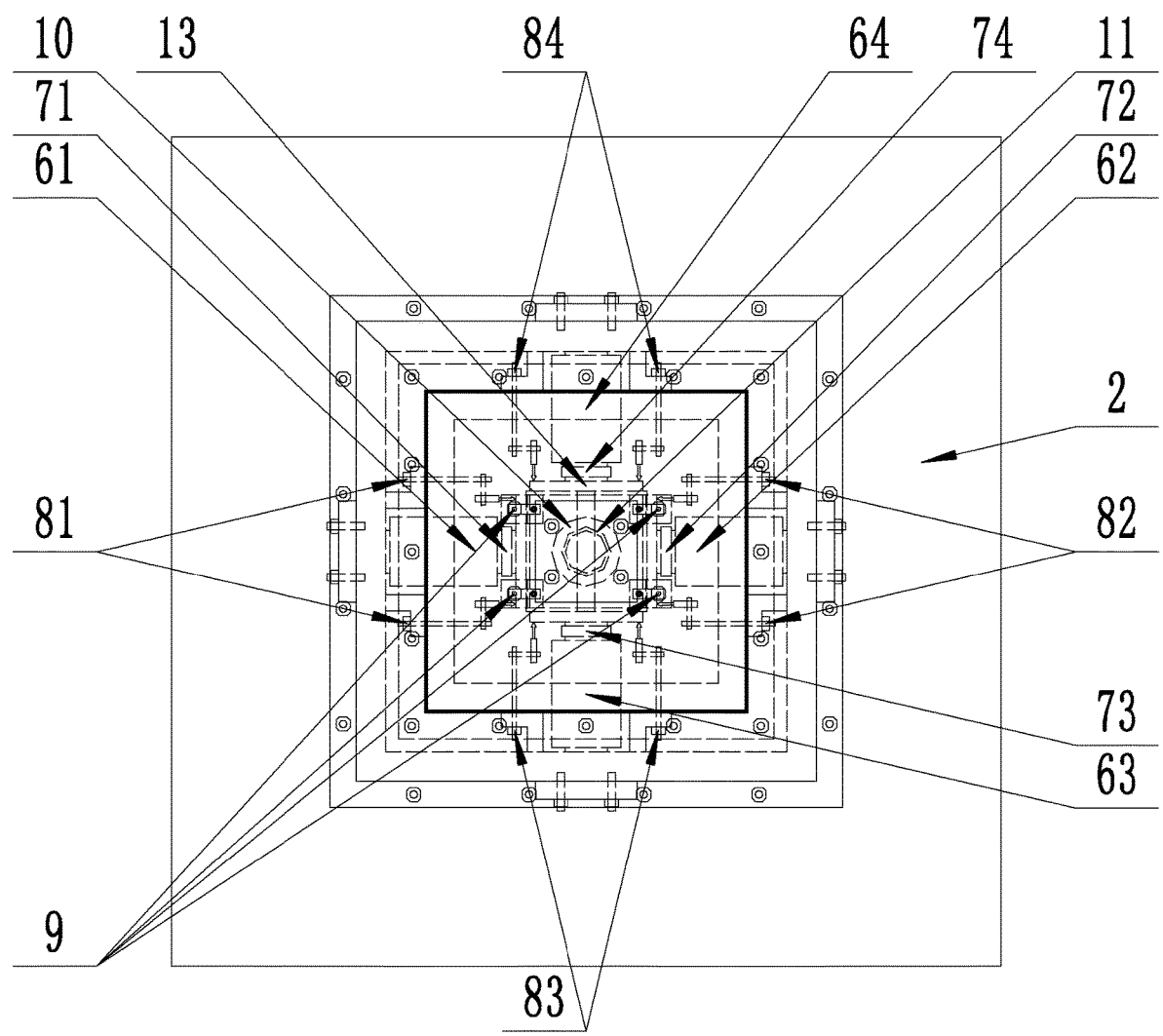
FIG. 2 is a top view of the test apparatus for simulating a seismic dynamic response of an underground cavern in the specific embodiment according to the present invention.

Referring to FIGS. 1 and 2, a front view and a top view of the test apparatus for simulating a seismic dynamic response of an underground cavern in a specific embodiment according to the present invention are shown. The test apparatus includes the loading frame 1, an underground cavern model composed of the overlying model 3 and the underlying model 4, a static loading device configured to simulate vertical and horizontal in-situ stresses of the model, a dynamic loading device configured to simulate a seismic dynamic load on the model and a measuring device configured to measure a load value and a deformation value of the model during the test. The static loading device is provided above the overlying model and on the peripheral side of the overlying model to apply a static load to the test model in a normal direction and different directions on the peripheral side. The dynamic loading device is provided under the underlying model to apply a dynamic load to the test model. The measuring device is correspondingly connected to the loading devices to measure the load value and the deformation value under different loading conditions in real time during the test to acquire highly reliable simulation test data of the seismic dynamic response of the underground cavern.

Further, the overlying model 3 is provided directly above the underlying model 4. The overlying model has a smaller size than the underlying model to constitute a convex structure. The overlying model and the underlying model are fixedly cemented by a model material. When the static loading device provided above the overlying model and on the peripheral side of the overlying model applies a static load to the model, the overlying model receives uniform and high-fidelity in-situ stress static loads in vertical and horizontal directions. When the dynamic loading device provided under the underlying model applies a dynamic load to the model, the underlying model receives a uniform and high-fidelity seismic dynamic load and transfers the seismic dynamic load to the overlying model to acquire high-fidelity simulation test data. It should be noted that in the prior art, the static loading and the dynamic loading are separately performed to separately acquire the relevant simulation data. Such a simulation method does not conform to the real situation of the underground cavern in nature, and acquires one-sided static loading test data or dynamic loading test data, which cannot be used as reference data for research in this field. In the present invention, the overlying model and the underlying model are integrated into an underground cavern model with a convex structure to realize the unification of static loading and dynamic loading of the model. In this way, the test model in the present invention satisfies the seismic dynamic loading conditions of the in-situ underground cavern under real vertical and horizontal in-situ stresses, and conforms to the real stress state of the underground cavern in nature. The present invention breaks through the research bottleneck in the prior art, and provides high-fidelity simulation test data for researchers in this field, which has significant implications for research in this field.

Further, according to a test objective and geometric, physical and mechanical parameters of the in-situ underground cavern, a similar material model of the underground cavern is prepared by taking fine iron powder, barite powder and quartz sand as aggregate materials and taking cement and gypsum as cementing materials.

Further, a hole for simulating the interior of the in-situ underground cavern is provided in the overlying model 3. The hole is a through hole. The cross section of the hole is circular, oval, horseshoe, rectangular or the like. The central axis of the preformed through hole and the central axis of the front and rear side plates of the loading frame 1 are parallel or intersect at a small angle (not exceeding 30°). The distance from the boundary of the preformed through hole to each of the upper boundary, the left boundary and the right boundary of the overlying model is greater than 6 times or more of the radius of the hole. A group of holes of different sizes, different shapes and different spatial distributions may be preformed in the overlying model to simulate a group of in-situ underground caverns. The distance from the boundary of the group of holes to each of the upper boundary, the left boundary and the right boundary of the overlying model is greater than 6 times or more of the radius of the largest hole in the group of holes. In an implementation of the present embodiment, the configuration of the hole is not limited.

Further, the dynamic loading device includes the model box 5, a bearing table and a dynamic load driving device for driving the model box and the bearing table to vibrate. The model box is provided on the bearing table. A chamber for receiving the underlying model 4 is provided inside the model box. In the present embodiment, the bearing table and the dynamic load driving device preferably adopt the shaking table 2.

Preferably, the model box 5, the loading frame 1 and the shaking table 2 are fixedly connected by bolts.

Preferably, the model box 5 is an uncovered cuboid steel box structure. The model box includes a left vertical plate, a right vertical plate, a front vertical plate, a rear vertical plate and a bottom plate.

Preferably, the underlying model 4 and the model box 5 have the same height, and the peripheral side of the underlying model and the model box are connected by silica gel. In the present embodiment, the underlying model is provided at the center of the model box. The space between the left, right, front and rear surfaces of the underlying model and the model box is filled with silica gel with a thickness that is 1-1.5% of the size of the underlying model to reduce the boundary effect of the rigid model box on the underlying model.

It should be noted that in the prior art, in order to reduce the boundary effect of a large-scale physical model test, a foam is typically filled between the model and the model box, but the foam is not effective when the model and the model box move toward each other. Instead, the silica gel can produce plastic flow when the model and the model box move relative to or toward each other to play a buffering role while effectively reducing the boundary effect.

Further, the loading frame 1 includes a top plate and side plates. The top plate and the side plates are made of steel. The side plates include a left side plate, a right side plate, a front side plate and a rear side plate. The upper ends of the left side plate, the right side plate, the front side plate and the rear side plate are fixedly connected to the top plate. The lower ends of the left side plate, the right side plate, the front side plate and the rear side plate are connected to the shaking table 2 by bolts. The left side plate, the right side plate, the front side plate and the rear side plate are arranged perpendicular to the shaking table. The left side plate and the right side plate of the loading frame are parallel to the left vertical plate and the right vertical plate of the model box 5, respectively. The top plate of the loading frame is vertically opposite to the bottom plate of the model box, and has a larger size than the bottom plate of the model box.

Further, the measuring device includes a load measuring device and a deformation measuring device. The load measuring device includes a normal load measuring device for measuring a load value of the top of the overlying model and a lateral load measuring device for measuring a load value of the peripheral side of the overlying model. Preferably, the normal load measuring device is the normal load sensor 11. The lateral load measuring device includes the left load sensor 71, the right load sensor 72, the front load sensor 73 and the rear load sensor 74.

Further, the deformation measuring device includes a normal deformation measuring device for measuring a deformation value of the top of the overlying model and a lateral deformation measuring device for measuring a deformation value of the peripheral side of the overlying model. Preferably, the normal deformation measuring device includes four normal deformation sensors 9 that are evenly distributed. The lateral deformation measuring device includes two left deformation sensors 81, two right deformation sensors 82, two front deformation sensors 83 and two rear deformation sensors 84.

Further, the static loading device includes a normal loading device and a lateral loading device. The normal loading device is provided on the top of the overlying model, and the upper end of the normal loading device is fixedly connected to a top plate of the loading frame. The normal loading device includes the normal cylinder 10 and the normal backing plate 12. The normal backing plate is a steel backing plate. The normal cylinder applies a force to the top of the overlying model through the normal backing plate. The normal load sensor 11 provided between the normal backing plate and the normal cylinder measures the vertical load in real time.

Preferably, the normal cylinder 10 is provided at the center of the top plate of the loading frame 1.

Further, the lateral loading device is provided on the peripheral side of the overlying model, and an end of the lateral loading device away from the overlying model is connected to a side plate of the loading frame. The lateral loading device includes a lateral cylinder and the lateral backing plate 13. The lateral backing plate is a steel backing plate. The lateral cylinder applies a force to the peripheral side wall of the overlying model through the lateral backing plate. The lateral load sensor provided between the lateral backing plate and the lateral cylinder measures the horizontal load in real time.

Preferably, the lateral cylinder includes the left cylinder 61, the right cylinder 62, the front cylinder 63 and the rear cylinder 64. The left cylinder, the right cylinder, the front cylinder and the rear cylinder are fixed at the centers of the left side plate, the right side plate, the front side plate and the rear side plate of the loading frame 1, respectively.

Preferably, the four normal deformation sensors 9 are symmetrically distributed around the normal cylinder 10. One end of the normal deformation sensor is fixedly connected to the top plate of the loading frame 1 through a bolt device, and the other end of the normal deformation sensor is in contact with the normal backing plate 12. These normal deformation sensors are configured to measure a vertical deformation of the overlying model under a normal load in real time. In the present invention, the vertical deformation value of the overlying model is the displacement value of the normal backing plate relative to the loading frame, that is, the normal deformation sensor records the relative displacement value of the normal backing plate in real time during the test.

Preferably, the two left deformation sensors 81, the two right deformation sensors 82, the two front deformation sensors 83 and the two rear deformation sensors 84 are symmetrically distributed on both sides of the left cylinder 61, the right cylinder 62, the front cylinder 63 and the rear cylinder 64, respectively. One end of each of the two left deformation sensors, the two right deformation sensors, the two front deformation sensors and the two rear deformation sensors is fixedly connected to the left side plate, the right side plate, the front side plate and the rear side plate of the loading frame 1, respectively by a bolt device. The other end of each of the two left deformation sensors, the two right deformation sensors, the two front deformation sensors and the two rear deformation sensors is in contact with the four lateral backing plates 13, respectively. These deformation sensors are configured to measure a horizontal deformation of the overlying model 3 under a lateral load in real time. In the present invention, a horizontal deformation value of the overlying model is a displacement value of the lateral backing plate relative to the loading frame, that is, the lateral deformation sensor records the relative displacement value of the lateral backing plate in real time during the test.

Preferably, the normal backing plate 12 and the lateral backing plate 13 have the same size that is smaller than the size of the overlying model 3. The center of the normal backing plate is vertically opposite to the center of the overlying model, and the center of the lateral backing plate is horizontally opposite to the center of the overlying model. In the present invention, the overlying model is uniformly stressed through the normal backing plate and the lateral backing plate.

Further, the test apparatus further includes a numerical control device. The numerical control device is connected to the normal cylinder, the normal load sensor, the normal deformation sensor, the lateral cylinder, the lateral load sensor, the lateral deformation sensor and the shaking table through a cable to acquire the load value and the deformation value of the overlying model measured by the normal load sensor, the lateral load sensor, the normal deformation sensor and the lateral deformation sensor in real time during the test.

Further, according to a test objective and geometric, physical and mechanical parameters of the in-situ underground cavern, a similar material model of the underground cavern is prepared by taking fine iron powder, barite powder and quartz sand as aggregate materials and taking cement and gypsum as cementing materials. Based on the similarity theory, the geometric, physical and mechanical parameters of the underground cavern model are calculated. Specifically, physical and mechanical parameters such as size, buried depth, elastic modulus, compressive strength, tensile strength, cohesion, stress and displacement between the in-situ underground cavern and the model each have a similarity relationship of n. Parameters such as density, acceleration, Poisson's ratio, internal friction angle, strain and acceleration of gravity between the in-situ underground cavern and the model each have a similarity relationship of 1. Parameters such as velocity and time between the in-situ underground cavern and the model each have a similarity relationship of $n^{0.5}$. Frequency and other parameters between the in-situ underground cavern and the model have a similarity relationship of $n^{-0.5}$.

Preferably, the similar material model of the underground cavern includes aggregate materials and cementing materials. The aggregate materials include 0-40% fine iron powder, 30-70% barite powder and 0-45% quartz sand. The cementing materials include 0-3.5% cement and 0-20% gypsum. Within the content ranges of these similar materials, when the surrounding rock of the in-situ underground cavern has a high density, the contents of the fine iron powder and the barite powder in the underground cavern model are increased while the content of the gypsum is reduced. When the surrounding rock of the in-situ underground cavern has high elastic modulus and compressive strength, the contents of the gypsum and the fine iron powder in the underground cavern model are increased while the content of the barite powder is reduced. When the surrounding rock of the in-situ underground cavern has a high shear strength, the contents of the gypsum and the cement are increased to increase the cohesion while the contents of the fine iron powder and the barite powder are reduced to increase the internal friction angle.

A method based on the test apparatus for simulating a seismic dynamic response of an underground cavern includes the following steps:

S100: a normal load value, a first horizontal load value, a second horizontal load value, a seismic dynamic load value, a seismic dynamic loading time value, a normal deformation threshold and a lateral deformation threshold are preset by a numerical control device; and a seismic dynamic load is applied by using any loading control modes including a ground acceleration mode, a loading time and ground velocity mode, a loading time or ground displacement mode, and a loading time mode.

S200: the normal cylinder is controlled by the numerical control device to apply a vertical load to the overlying model and keep the vertical load constant to simulate a real vertical in-situ stress of an in-situ underground cavern.

S300: the front cylinder and the rear cylinder are controlled by the numerical control device to separately apply a same first horizontal load to the overlying model and keep the first horizontal load constant to simulate a real larger horizontal in-situ stress of the in-situ underground cavern.

S400: the left cylinder and the right cylinder are controlled by the numerical control device to separately apply a same second horizontal load to the overlying model and keep the second horizontal constant to simulate a real smaller horizontal in-situ stress of the in-situ underground cavern.

S500: the dynamic load driving device is controlled by the numerical control device to apply a seismic dynamic load to the underlying model, and the seismic dynamic load acts on the overlying model through the underlying model to simulate a real seismic ground motion on the in-situ underground cavern.

S600: the numerical control device performs real-time control on the test based on a load value and a deformation value of the overlying model acquired in real time by the normal load sensor, the lateral load sensor, the normal deformation sensor and the lateral deformation sensor during the test; the test is stopped and load and deformation data are exported for analysis when a seismic dynamic loading time reaches the preset value or when a normal deformation value of the overlying model of the underground cavern model reaches one half of a difference between the size of a lateral backing plate and the size of the overlying model or a unilateral deformation value of the overlying model reaches one half of a difference between the size of a normal backing plate and the size of the overlying model.

It should be noted that based on the structural design of the above-mentioned test apparatus, according to the in-situ stresses and seismic loads of the in-situ underground cavern, this method is based on the similarity theory to calculate the vertical load, horizontal load and seismic dynamic load acting on the underground cavern model, and acquires high-fidelity simulation test data of the seismic dynamic response of the underground cavern.

Further, in the present embodiment, the sequence of step S300 and step S400 can be flexibly set according to actual conditions. According to the principle that the axis of the in-situ underground cavern and the maximum principal stress are preferably parallel or intersect at a small angle, the first horizontal load is a larger horizontal load to simulate a real larger horizontal in-situ stress of the in-situ underground cavern, while the second horizontal load is a smaller horizontal load to simulate a real smaller horizontal in-situ stress of the in-situ underground cavern. It should be noted that, in general, the first horizontal load and the second horizontal load are about 1.0-1.5 times the vertical load. If the larger horizontal load is 1.5 times the vertical load, the smaller horizontal load is about 1.0-1.5 times the vertical load. Under in-situ conditions, the vertical load is generally 0.0278 of the buried depth of the underground cavern. For example, for an underground cavern with a buried depth of 1000 m, the vertical load is about 27.8 MPa.

Although the present invention is described with reference to the preferred embodiments, various modifications may be made to the present invention and the components therein may be replaced with equivalents without departing from the scope of the present invention. In particular, the various technical features mentioned in the various embodiments may be combined in any manner in case of no structural conflict. The present invention is not limited to the specific embodiments disclosed herein, but includes all technical solutions falling within the scope of the claims.

It should be noted that in the description of the present invention, terms such as "central/center", "upper", "lower", "left", "right", "vertical", "horizontal", "inner/inside" and "outer/outside" indicate orientation or position relationships based on the drawings. These terms are merely intended to facilitate description, rather than to indicate or imply that the mentioned device or components must have the specific orientation and must be constructed and operated in the specific orientation, and thus should not be construed as a limitation to the present invention. Moreover, the terms "first", "second", "third" and the like are used only for the purpose of description, rather than to indicate or imply relative importance.

It should be noted that in the description of the present invention, unless otherwise clearly specified, the meanings of terms "install", "connected to" and "connection" should be understood in a broad sense. For example, the connection may be a fixed connection, a removable connection, or an integral connection; may be a mechanical connection or an electrical connection; may be a direct connection or an indirect connection via a medium; or may be an internal connection between two components. Those skilled in the art should understand the specific meanings of the above terms in the present invention based on specific situations.

In addition, terms "include/comprise", or any other variations thereof are intended to cover non-exclusive inclusions, so that a process, an article, or a device/apparatus including a series of elements not only includes those elements, but also includes other elements that are not explicitly listed, or further includes elements inherent in the process, article or device/apparatus.

Hereto, the technical solutions of the present invention have been described with reference to the preferred implementations and drawings. Those skilled in the art should easily understand that the scope of protection of the present invention is apparently not limited to these specific implementations. Those skilled in the art can make equivalent changes or substitutions to the relevant technical features without departing from the principles of the present invention, and the technical solutions obtained based on these changes or substitutions shall fall within the scope of protection of the present invention.

What is claimed is:

1. A test apparatus for simulating a seismic dynamic response of an underground cavern, comprising
    a loading frame, an underground cavern model, a static loading device, a dynamic loading device and a measuring device;
    wherein
    the test apparatus is configured to perform a high-fidelity simulation on the underground cavern through unified loading of an in-situ stress static load and a seismic dynamic load;
    the underground cavern model comprises an overlying model and an underlying model; wherein
        the overlying model is provided on a top of the underlying model; the overlying model and the underlying model constitute a convex structure; the overlying model and the underlying model are fixedly cemented;
    the static loading device comprises a normal loading device and a lateral loading device; wherein
        the normal loading device is provided on a top of the overlying model, and an upper end of the normal loading device is fixedly connected to a top plate of the loading frame;
        the normal loading device comprises a normal driving device and a normal backing plate; wherein
            the normal driving device applies a force to the top of the overlying model through the normal backing plate;
        the lateral loading device is provided on a peripheral side of the overlying model, and an end of the lateral loading device away from the overlying model is fixedly connected to a side plate of the loading frame;
        the lateral loading device comprises a lateral driving device and a lateral backing plate; wherein
            the lateral driving device applies a force to a peripheral side wall of the overlying model through the lateral backing plate;
    the dynamic loading device comprises a model box, a bearing table and a dynamic load driving device for driving the model box and the bearing table to vibrate; wherein
        the model box is provided on the bearing table; a chamber for receiving the underlying model is provided inside the model box; the underlying model and the model box have the same height, and a peripheral side of the underlying model is connected to the model box by silica gel;
    the measuring device comprises a load measuring device and a deformation measuring device; wherein
        the load measuring device comprises a normal load measuring device for measuring a load value of the top of the overlying model and a lateral load measuring device for measuring a load value of the peripheral side of the overlying model;
        the deformation measuring device comprises a normal deformation measuring device and a lateral deformation measuring device; wherein
            the normal deformation measuring device is configured to measure a displacement value of the normal backing plate relative to the loading frame in real time; and
            the lateral deformation measuring device is configured to measure a displacement value of the lateral backing plate relative to the loading frame.

2. The test apparatus for simulating the seismic dynamic response of the underground cavern according to claim 1, wherein
    a hole for simulating an in-situ underground cavern is provided in the overlying model, and the hole is a through hole.

3. The test apparatus for simulating the seismic dynamic response of the underground cavern according to claim 2, further comprising a numerical control device; wherein
    the numerical control device is communicatively connected to the static loading device and the dynamic loading device, and
    the numerical control device is configured to record the load value of the top of the overlying model, the load value of the peripheral side of the overlying model and a deformation value of the underground cavern model in real time.

4. The test apparatus for simulating the seismic dynamic response of the underground cavern according to claim 1, wherein
    the normal load measuring device is a normal load sensor, and the lateral load measuring device is a lateral load sensor;
    the normal backing plate is a first steel backing plate; and the lateral backing plate is a second steel backing plate.

5. The test apparatus for simulating the seismic dynamic response of the underground cavern according to claim 4, wherein
    the normal driving device is a normal cylinder, and the normal cylinder is fixed at a center of the top plate of the loading frame;

the lateral driving device is a lateral cylinder; the lateral cylinder comprises a left cylinder, a right cylinder, a front cylinder and a rear cylinder; and the left cylinder, the right cylinder, the front cylinder and the rear cylinder are fixed at centers of a left side plate, a right side plate, a front side plate and a rear side plate of the loading frame, respectively.

6. The test apparatus for simulating the seismic dynamic response of the underground cavern according to claim 5, wherein the normal deformation measuring device is normal deformation sensors; first ends of the normal deformation sensors are fixed to a top of the loading frame, and second ends of the normal deformation sensors are in contact with the normal backing plate;

the number of the normal deformation sensors is four, and the four normal deformation sensors are symmetrically arranged around the normal cylinder;

the lateral deformation measuring device is lateral deformation sensors; first ends of the lateral deformation sensors are fixed to the side plate of the loading frame, and second ends of the lateral deformation sensors are in contact with the lateral backing plate;

the lateral deformation sensors comprise two left deformation sensors, two right deformation sensors, two front deformation sensors and two rear deformation sensors;

the two left deformation sensors, the two right deformation sensors, the two front deformation sensors and the two rear deformation sensors are symmetrically arranged on both sides of the left cylinder, both sides of the right cylinder, both sides of the front cylinder and both sides of the rear cylinder, respectively, and the two left deformation sensors, the two right deformation sensors, the two front deformation sensors and the two rear deformation sensors are configured to measure deformation values of a left side, a right side, a front side and a rear side of the overlying model, respectively.

7. The test apparatus for simulating the seismic dynamic response of the underground cavern according to claim 6, further comprising a numerical control device; wherein the numerical control device is communicatively connected to the static loading device and the dynamic loading device, and the numerical control device is configured to record the load value of the top of the overlying model, the load value of the peripheral side of the overlying model and a deformation value of the underground cavern model in real time.

8. The test apparatus for simulating the seismic dynamic response of the underground cavern according to claim 5, further comprising a numerical control device; wherein the numerical control device is communicatively connected to the static loading device and the dynamic loading device, and the numerical control device is configured to record the load value of the top of the overlying model, the load value of the peripheral side of the overlying model and a deformation value of the underground cavern model in real time.

9. The test apparatus for simulating the seismic dynamic response of the underground cavern according to claim 4, further comprising a numerical control device; wherein the numerical control device is communicatively connected to the static loading device and the dynamic loading device, and the numerical control device is configured to record the load value of the top of the overlying model, the load value of the peripheral side of the overlying model and a deformation value of the underground cavern model in real time.

10. The test apparatus for simulating the seismic dynamic response of the underground cavern according to claim 1, wherein the model box is an uncovered cuboid steel box structure; and the model box and the bearing table are fixedly connected by a bolt.

11. The test apparatus for simulating the seismic dynamic response of the underground cavern according to claim 10, further comprising a numerical control device; wherein the numerical control device is communicatively connected to the static loading device and the dynamic loading device, and the numerical control device is configured to record the load value of the top of the overlying model, the load value of the peripheral side of the overlying model and a deformation value of the underground cavern model in real time.

12. The test apparatus for simulating the seismic dynamic response of the underground cavern according to claim 1, further comprising a numerical control device; wherein the numerical control device is communicatively connected to the static loading device and the dynamic loading device, and the numerical control device is configured to record the load value and a deformation value of the underground cavern model in real time.

13. A test method for simulating a seismic dynamic response of an underground cavern based on the test apparatus for simulating the seismic dynamic response of the underground cavern according to claim 12, comprising the following steps:

S100: presetting a normal load value, a first horizontal load value, a second horizontal load value, a seismic dynamic load value, a seismic dynamic loading time value, a normal deformation threshold and a lateral deformation threshold;

S200: controlling the normal driving device to apply a vertical load to the overlying model and keep the vertical load constant to simulate a real vertical in-situ stress of the in-situ underground cavern;

S300: controlling a front cylinder and a rear cylinder of the lateral driving device to separately apply a first horizontal load to the overlying model and keep the first horizontal load constant;

S400: controlling a left cylinder and a right cylinder of the lateral driving device to separately apply a second horizontal load to the overlying model and keep the second horizontal load constant;

S500: controlling the dynamic load driving device to apply the seismic dynamic load to the underlying model and allowing the seismic dynamic load to act on the overlying model through the underlying model to simulate a real seismic ground motion on the in-situ underground cavern; and S600: performing, by the numerical control device, real-time control on a test based on the load value and the deformation value of the overlying model acquired in real time by the normal load measuring device, the lateral load measuring device, the normal deformation measuring device and the lateral deformation measuring device during the test; stopping the test and exporting load and deformation test data when a seismic dynamic loading time reaches the seismic dynamic loading time value or when a normal deformation value of the overlying model of the underground cavern model reaches one half of a difference between a size of the lateral backing plate and a size of the overlying model or when a unilateral deformation value of the overlying model reaches one half of a difference between a size of the normal backing plate and a size of the overlying model.

* * * * *